(12) United States Patent
Sundell

(10) Patent No.: US 8,537,294 B2
(45) Date of Patent: Sep. 17, 2013

(54) AUTOMATIC DARKENING FILTER APPARATUS AND METHOD

(71) Applicant: 3M Innovative Properties Company, St. Paul, MN (US)

(72) Inventor: Ingvar Sundell, Laksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/747,541

(22) Filed: Jan. 23, 2013

(65) Prior Publication Data

US 2013/0128135 A1    May 23, 2013

Related U.S. Application Data

(62) Division of application No. 12/681,672, filed as application No. PCT/US2008/075089 on Sep. 3, 2008, now Pat. No. 8,384,855.

(60) Provisional application No. 60/977,701, filed on Oct. 5, 2007.

(51) Int. Cl.
*G02F 1/1335* (2006.01)

(52) U.S. Cl.
USPC .............................. 349/16; 349/96

(58) Field of Classification Search
USPC ......................................................... 349/96
See application file for complete search history.

(56) References Cited

U.S. PATENT DOCUMENTS

| | | | |
|---|---|---|---|
| 5,208,688 A | 5/1993 | Fergason et al. | |
| 5,248,880 A | 9/1993 | Fergason | |
| 5,377,032 A | 12/1994 | Fergason et al. | |
| 5,519,522 A | 5/1996 | Fergason | |
| 5,751,258 A | 5/1998 | Fergason et al. | |
| 6,070,264 A | 6/2000 | Hamilton et al. | |
| 6,614,409 B1 | 9/2003 | Bae | |
| 6,881,939 B1 | 4/2005 | Hamilton et al. | |
| 6,884,987 B2 | 4/2005 | Hamilton et al. | |
| 7,005,624 B2 | 2/2006 | Hamilton | |
| 7,008,055 B2 | 3/2006 | McLear et al. | |
| 7,161,135 B2 | 1/2007 | Fergason | |
| 7,232,988 B2 | 6/2007 | Hamilton et al. | |
| 2003/0206491 A1 | 11/2003 | Pacheco et al. | |
| 2005/0007667 A1 | 1/2005 | Fergason | |
| 2006/0203148 A1 | 9/2006 | Magnusson et al. | |

FOREIGN PATENT DOCUMENTS

| | | |
|---|---|---|
| CN | 2 662 865 | 12/2004 |
| WO | WO 91/09337 A1 | 6/1991 |
| WO | WO 92/14183 A1 | 8/1992 |
| WO | WO 2005/051254 | 9/2005 |
| WO | WO 2007001777 | 1/2007 |

OTHER PUBLICATIONS

Supplementary European Search Report, PCT/US2008/075089, Sep. 29, 2010, 3 pages.

*Primary Examiner* — Phu Vu
(74) *Attorney, Agent, or Firm* — Kenneth B. Wood

(57) ABSTRACT

Herein is disclosed an automatic darkening filter apparatus comprising a shutter control system configured to cause a shutter to switch from a dark state to an intermediate state in response to a change from high intensity incident light to low intensity incident light being detected. The control system is further configured to maintain the shutter in the intermediate state for a period of time, unless during this period of time high intensity light is detected, in which case the control system causes the shutter to switch to the dark state. If, at the end of the period of time, high intensity light is not detected, the shutter is caused to switch from the intermediate state to a light state.

19 Claims, 4 Drawing Sheets

AUTOMATIC DARKENING FILTER APPARATUS AND METHOD

This application is a divisional of U.S. patent application Ser. No. 12/681,672, now allowed, which application was a national stage filing under 35 U.S.C. 371 of PCT Application No. PCT/US2008/075089 filed 3 Sep. 2008, which claims priority to U.S. Provisional Application No. 60/977,701, filed 5 Oct. 2007; the disclosures of which are incorporated by reference in their entirety herein.

BACKGROUND

Automatic darkening filters are often provided on protective gear (e.g., headwear or eyewear), where protection from high intensity light is desired. An automatic darkening filter often includes a shutter that is capable of assuming a dark state and a light state, and a shutter control system that can cause the shutter to assume a dark state when subject to high intensity light and to assume a light state when not subject to high intensity light. Automatic darkening filters and related apparatus are described in, for example, U.S. Pat. No. 5,208,688 to Fergason et al., U.S. Pat. No. 5,248,880 to Fergason, U.S. Pat. No. 6,070,264 to Hamilton et al., U.S. Pat. No. 6,881,939 to Hamilton and Scott, and U.S. Pat. No. 7,008,055 to McLear and Gerfin.

SUMMARY

Automatic darkening filters are often designed to exhibit rapid response to changes in incident light intensity, in order to protect the eyesight of the user, particularly during operations that involve intermittent exposure to high intensity light. Applicant has determined that some users can perceive such rapid, abrupt optical transitions as undesirable, especially under conditions where many such transitions are experienced. Herein is thus disclosed an automatic darkening filter apparatus that is capable of avoiding an abrupt transition of a shutter from a dark state to a light state.

The automatic darkening filter apparatus disclosed herein comprises a switchable shutter that is capable of assuming a dark state, a light state, and at least one intermediate state. The automatic darkening filter apparatus further comprises a shutter control system operatively connected to the shutter and comprising a detector that is capable of detecting at least a "high" input (signal) that is indicative of a high intensity of incident light, and a "low" input that is indicative of a low intensity of incident light.

The control system is configured to switch the shutter immediately to a dark state if a change from low input to high input is detected by the control system, and to maintain the shutter in a dark state upon continued detection of high input. The control system is further configured to switch the shutter to an intermediate state if a change from high input to low input is detected by the control system. The control system is further configured to maintain the shutter in the intermediate state for a predetermined period of time $T_1$, unless during period of time $T_1$ a change from low input to high input is detected, in which case the control system switches the shutter immediately to the dark state. If, at the end of period of time $T_1$, the control system detects a low input, the control system switches the shutter to a light state.

Such a stepwise change of the shutter from a dark state to a light state (that is, by maintaining the shutter in an intermediate state for a period of time $T_1$ during the transition from a dark state to a light state) can serve to minimize any discomfort that may perceived by a user to be caused by abrupt dark state to light state transitions. The use of such an intermediate state may be particularly beneficial in applications in which a user is exposed to intermittent high intensity light (e.g. operations such as welding, in particular spot-welding, in which there are frequent brief interruptions). In such a circumstance, rather than the shutter switching fully from a dark state to a light state during each interruption, the shutter may only switch from a dark state to an intermediate state, thus minimizing any perceived discomfort that might result from experiencing such repeated full changes in shutter opacity.

In one embodiment, the shutter control system is configured such that when a change from high input to low input is detected, the shutter is held in the dark state for a predetermined period of time $T_2$. If, at the end of period of time $T_2$, the control system still detects low input, the control system switches the shutter to an intermediate state. The control system then maintains the shutter in the intermediate state as described above, and either switches the shutter to a dark state if a change to high input is detected during time period $T_1$, or switches the shutter to a light state at the end of time period $T_1$ if low input is still being detected at the end of time period $T_1$.

In one aspect, herein is disclosed a method for controlling a switchable shutter capable of assuming a light state, a dark state and at least one intermediate state, by the use of a shutter control system operatively connected to the shutter and capable of detecting at least high input and low input and changes therebetween, the method comprising: i) switching the shutter from a dark state to an intermediate state if a change from high input to low input is detected; ii) maintaining the shutter in the intermediate state for a predetermined period of time $T_1$ of at least about 100 milliseconds if low input continues to be detected during period of time $T_1$; iii) switching the shutter from the intermediate state to a light state at the end of period of time $T_1$ if low input is detected at the end of period of time $T_1$; and, a) switching the shutter to a dark state if a change from low input to high input is detected, b) maintaining the shutter in a dark state if high input continues to be detected. In a further embodiment of this method, step i) comprises maintaining the shutter in a dark state for a predetermined period of time $T_2$ of greater than about 20 milliseconds if a change from high input to low input is detected, then switching the shutter from the dark state to an intermediate state. In another embodiment of the method, at least steps i), a) and b) are carried out repeatedly during the course of exposure of the shutter to intermittent high intensity light.

In another aspect, herein is disclosed an automatic darkening filter apparatus comprising a switchable shutter capable of assuming a dark state, a light state, and at least one intermediate state; and, a shutter control system operatively connected to the shutter and capable of detecting at least high input and low input and changes therebetween, wherein the shutter control system is configured to: switch the shutter from a dark state to an intermediate state if a change from high input to low input is detected; maintain the shutter in the intermediate state for a predetermined period of time $T_1$ of at least about 100 milliseconds if low input continues to be detected during period of time $T_1$; switch the shutter from the intermediate state to a light state at the end of period of time $T_1$ if low input is detected at the end of period of time $T_1$; switch the shutter to a dark state if a change from low input to high input is detected; maintain the shutter in the dark state if high input continues to be detected. In a further embodiment of this apparatus, the shutter control system is configured to maintain the shutter in a dark state for a predetermined period of time $T_2$ of greater than about 20 milliseconds if a change from high input to low input is detected, before switching the shutter from the dark state to an intermediate state.

These and other aspects of the invention will be apparent from the detailed description below. In no event, however, should the above summaries be construed as limitations on the claimed subject matter, which subject matter is defined solely by the attached claims, as may be amended during prosecution.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings.

DETAILED DESCRIPTION

Although terms such as "top", bottom", "upper", lower", "front" and "back", and "first" and "second" may be used in this disclosure, it should be understood that those terms are used in their relative sense only.

Figure 1:
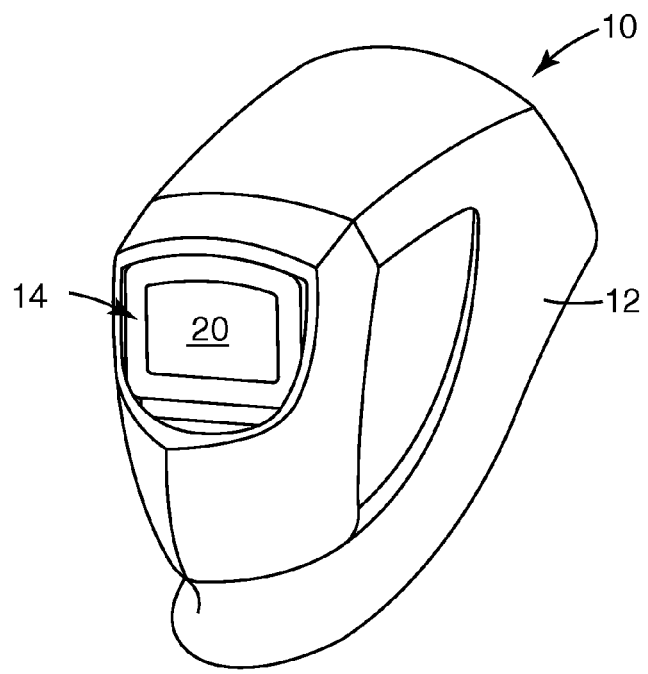
FIG. 1 is a perspective view of one embodiment of an automatic darkening filter apparatus, mounted on a protective shield.

Herein is disclosed an automatic darkening filter apparatus and method of operation. Such an automatic darkening filter apparatus can be included in protective headgear, for example shield (e.g. safety shield, also known as helmet) 10 illustrated in FIG. 1. Shield 10 includes shield body 12 and automatic darkening filter apparatus 14 in shield body 12. Automatic darkening filter apparatus 14 includes switchable shutter 20 that is placed in position to intercept electromagnetic radiation (e.g., visible light, UV light, IR, etc.) Preferably, shutter 20 is positioned in shield body 12 so that it is directly in front of the wearer's eyes when the shield is worn by the user.

In various embodiments, one or more automatic darkening filter apparatuses 14 may be provided in any other suitable equipment or articles and for other applications. For example, automatic darkening filter apparatus 14 may be supplied as part of protective eyewear (e.g. goggles) rather than the full-coverage shield of FIG. 1. Or, automatic darkening filter apparatus 14 may be provided in a hand held device. Or, automatic darkening filter apparatus 14 may be provided in a window or aperture allowing inspection of a room, enclosure, machinery space etc., in which high intensity light may be present.

Automatic darkening filter apparatus 14 can be used in connection with industrial operations, for example welding (e.g. arc welding, torch welding, acetylene welding), cutting (e.g. laser cutting, acetylene cutting), brazing, soldering and the like. It can also be used in connection with medical procedures involving high intensity light (e.g. laser surgery, hair removal, tattoo removal, light-curing of dental resins, etc.). Many other uses are possible.

Figure 2:
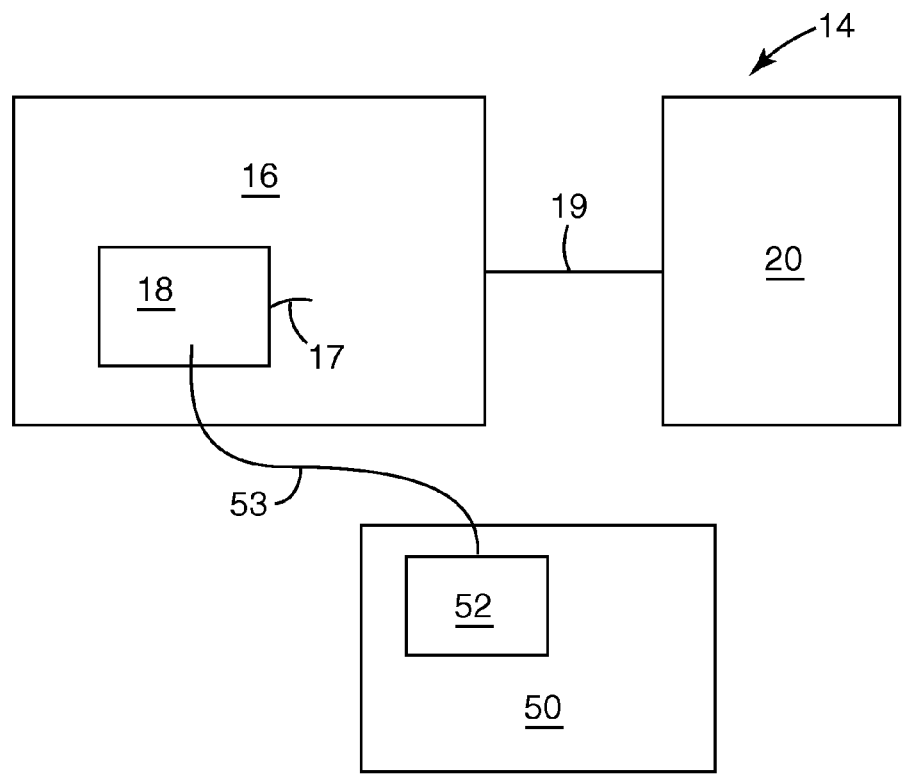
FIG. 2 is a block diagram of one embodiment of an automatic darkening filter apparatus.

With reference to the block diagram of FIG. 2, automatic darkening filter apparatus 14 comprises at least a switchable shutter 20, and a shutter control system 16 that comprises a detector 18.

In one embodiment, automatic darkening filter apparatus 14 is configured to block high intensity light. In this context, "light" means electromagnetic radiation of a wavelength that might be capable of damaging the eyes of a user, or of causing perceived discomfort to the user. In this context, such light includes at least visible light, and may also include infrared and/or ultraviolet radiation, whether or not such radiation is perceptible to the user. In this context, "high intensity" light means light that is present at such intensity (e.g. such as that emitted by a device such as an arc welder) such that it might be capable of damaging the eyes of a user, or of causing perceived discomfort to the user.

The term switchable shutter (also called a lens or filter) denotes a device that can controllably affect the intensity of electromagnetic energy that is being transmitted through the shutter. In various embodiments, shutter 20 can comprise one or more liquid crystal layers. In other embodiments, shutter 20 can comprise a combination of layers of liquid crystals and polarizing filters, as described in, for example, U.S. Patent Application Publication 2006/0203148 A1 to Magnusson et al. In other embodiments, shutter 20 may be constructed using electrochromic materials.

Switchable shutter 20 is capable of assuming a dark state, a light state, and at least one intermediate state, and of being switched therebetween. In this context, a dark state means that the shutter is in a nearly opaque state in which the majority of incident light is blocked. Thus, only in the case that the incident light is of high intensity does any light penetrate the shutter. A light state means that the shutter is in a nearly clear or transparent state such that (low intensity) ambient light is capable of penetrating the shutter. An intermediate state means that the shutter is in a state of opacity that is between the light and dark states. The intermediate state is a transitional state that shutter 20 will only remain in for limited periods of time (each period will be no longer than predetermined length of time $T_1$, as discussed in detail later herein.) As discussed above, one purpose of the intermediate state is to provide a stepwise transition when the shutter is switched from a dark state to a light state. (Typically, the intermediate state will not be used when the shutter is switched from a light state to a dark state, since, for reasons of safety, this transition should occur as rapidly as possible.)

The amount of incident light transmitted by shutter 20 in the various states can be characterized in various ways. One way commonly used in the art is the visible light transmission of the shutter. In various embodiments, shutter 20 is configured so as to exhibit a visible light transmission of less than about 0.5%, less than about 0.1%, or less than about 0.05%, when in a dark state; and, to exhibit a visible light transmission of greater than about 10%, greater than about 20%, or greater than about 50%, when in a light state. In various embodiments the visible light transmission of shutter 20 when in an intermediate state may be less than about 10%, less than about 5%, or less than about 2%, and may be greater than about 0.5%, greater than about 1%, or greater than about 1.5%. Other ranges are possible. Regardless of the ranges chosen, for a given shutter 20, the visible light transmission of the shutter in the intermediate state will always be higher than that of the shutter in the dark state and lower than that of the shutter in the light state.

Performance of shutter 20 may also be characterized by the Shade Number which is also commonly known in the art. Thus, in various embodiments shutter 20 may exhibit a Shade Number of greater than about 8, greater than about 10, or greater than about 12, when in a dark state; and, may exhibit a Shade Number of less than about 5, less than about 4, or less than about 3, when in a clear state. In various embodiments the Shade Number of shutter 20 when in an intermediate state may be less than about 8, less than about 7 or less than about 6, and may be greater than about 3, greater than about 4, or greater than about 5. (Regardless of the ranges chosen, for a given shutter 20, the Shade Number of the shutter in the intermediate state will always be higher than that of the shutter in the light state and lower than that of the shutter in the dark state).

Shutter 20 is capable of controllably blocking visible light. Shutter 20 may also be capable of adjustably (controllably) blocking infrared radiation and/or ultraviolet radiation. Or, components (e.g. additives within shutter 20, and/or separate layers in the light path) may be provided that always block (whether by absorption, reflection, scattering, or some other mechanism) such radiation. For example, ultraviolet-blocking coatings, infrared-blocking coatings, interference filters, and the like, may be provided as part of automatic darkening filter apparatus 14, either as part of, or in addition to, shutter 20.

Automatic darkening filter apparatus 14 comprises shutter control system 16 that is operatively connected to (e.g., capable of applying control signals to by way of connection 19) shutter 20. Thus, shutter control system 16 can switch shutter 20 between the various states (light, dark, and intermediate) by the use of any convenient control signal; for example, by varying a voltage that is applied to shutter 20. Upon a change in a control signal (e.g., voltage) being applied by shutter control system 16, shutter 20 typically exhibits a response time in lighter-to-darker transitions of less than one millisecond, and a response time in darker-to-lighter transitions of around a few milliseconds. When a constant value of a control signal is applied, shutter 20 typically exhibits a relatively constant light transmission. Thus, in one embodiment, shutter 20 comprises a relatively constant light transmission (e.g., as measured by visible light transmission, Shade Number, etc.) during time period $T_1$ that shutter 20 is held in the intermediate state.

Shutter control system 16 comprises input detector 18. Detector 18 is capable of detecting at least: "high" input that indicates the presence of high light intensity, "low" input that indicates the absence of high light intensity, a change from high to low input, and a change from low to high input. Detector 18 is also capable of communicating the detection of such high and low input and changes therebetween to the other components of shutter control system 16. As such, when expressions are used in this disclosure such as detects high input, detects low input, detects a change from high input to low input, etc., it will be understood that such detection is by way of detector 18 of control system 16.

In various embodiments, detector 18 may be located physically close to some or all of the other components (hardware, etc.) of shutter control system 16 or may be located physically remote from some or all of the other components. Regardless, detector 18 is in communication with other components of system 16 via connection 17 (which may be a dedicated wire, an optical fiber, a wireless connection, etc.), as needed for functioning of system 16.

In one embodiment, detector 18 is capable of directly detecting incident light of high intensity (e.g., detector 18 comprises a photosensitive device, including but not limited to a photodiode, phototransistor, and so on). In this instance, "high input" means that detector 18 is directly sensing incident light of high intensity. (In such an embodiment, it may be preferential to locate detector 18 in close proximity to shutter 20, so that the light incident on detector 18 is closely representative of the light incident on shutter 20).

In an alternative embodiment, detector 18 is capable of detecting the high light intensity indirectly. In such a case a high input can comprise an input that is indicative of the presence of a high light intensity. In a particular embodiment, detector 18 is in communication with a (potentially) light-emitting device 50 and is capable of receiving a high input from device 50 that indicates that device 50 is in a condition (e.g., powered up and operating) that is likely to emit high light intensity. In this context, a high input can comprise any signal sent via connection 53 (whether a dedicated wire, an optical fiber, a wireless connection, an IR signal, a radiofrequency broadcast, and the like) that can be received by detector 18 and that indicates that device 50 is in a condition that is likely to emit high light intensity. In such an arrangement, light emitting device 50 may include communication unit 52 that is capable of performing such communication with detector 18 via connection 53. If desired, such an arrangement can include a provision for two-way communication such that device 50 can receive an acknowledgement from automatic darkening filter apparatus 14 that apparatus 14 is functional, prior to device 50 emitting light.

In one embodiment, system 16 can use both types of detection (direct sensing of high intensity light, as well as receiving signals sent by light emitting device 50).

Detector 18 is also capable of detecting a "low" input. In various embodiments, a low input can be detected positively, or can be detected negatively. In an embodiment comprising direct positive detection, detector 18 can comprise a photosensitive device that is capable of detecting that a low intensity of light is present. In an alternative embodiment comprising indirect positive detection, detector 18 can comprise a communication device that can receive a "low" input from light-emitting device 50 (that is, a signal from device 50 that indicates that device 50 is not emitting high intensity light).

In the embodiment comprising negative detection of low input, a low input can comprise the absence of a high input (i.e., a low intensity of incident light is not directly detected but rather is inferred from the absence of a high input). In an embodiment comprising direct negative detection, detection of low input can comprise the non-detection of high intensity light by detector 18 (for example, if detector 18 is configured to be capable of detecting light only above a certain threshold intensity). In an alternative embodiment comprising indirect negative detection, detection of low input can comprise the non-detection by detector 18 of a signal from device 50 that indicates that device 50 is emitting high intensity light.

In various embodiments, detector 18 is configured to monitor input continuously, or intermittently. If intermittent monitoring is utilized, it is preferably done at sufficiently high frequency to enable sufficiently rapid response of apparatus 14.

Shutter control system 16 is configured to detect high or low input and changes therebetween (by way of detector 18) and to control shutter 20 accordingly. That is, system 16 is configured to switch shutter 20 between various states, and/or to maintain shutter 20 in a particular state for a predetermined time or an indefinite time, as described in detail herein, by way of sending a control signal (e.g. voltage) to shutter 20 via connection 19. Shutter control system 16 can comprise (in addition to detector 18) various hardware, electronic, software and/or firmware components, integrated circuits, power sources, etc., as are needed to fully carry out the functioning of system 16. In various embodiments, shutter control system 16 may be located close to shutter 20 (e.g., contained in the same physical casing or housing); alternatively, shutter control system 16 may be located physically remote from shutter 20. In either case, shutter control system 16 is operatively connected to shutter 20 via connection 19, which may be a dedicated wire, an optical fiber, a wireless connection, etc.

Shutter control system 16 is capable of performing several operations. These operations are described with reference to the flowcharts illustrated in FIGS. 3 and 4. These flowcharts are only exemplary representations to aid in understanding of processes that may be used, and useful, with the present invention. Other representations of the same or other processes that yield the same or similar functional results are also possible.

In these flowcharts, the rectangular symbols depict input-detection/shutter-control operations of system 16. For example, a label of "low input" in a rectangular symbol means that system 16 has just detected (by way of detector 18), or continues to detect, a low input. The oval symbols signify the state that shutter 20 is switched to, and/or maintained in, by system 16 as the result of an input-detection/shutter-control operation.

The diamond symbols depict waiting operations of shutter control system 16. Such a waiting operation can comprise waiting for a predetermined (i.e., specified) period of time (e.g. "Wait $T_1$" or "Wait $T_2$"); or, waiting for an indefinite period of time (e.g. "Wait", with no time specified). The diamond symbols further comprise decision-making paths that can be followed by system 16 based on the input, and changes thereof, that are provided by detector 18. Such decision-making paths can be followed during, or at the end of, a definite time period (e.g. $T_1$ or $T_2$); or, during an indefinite time period, as explained below.

Figure 3:
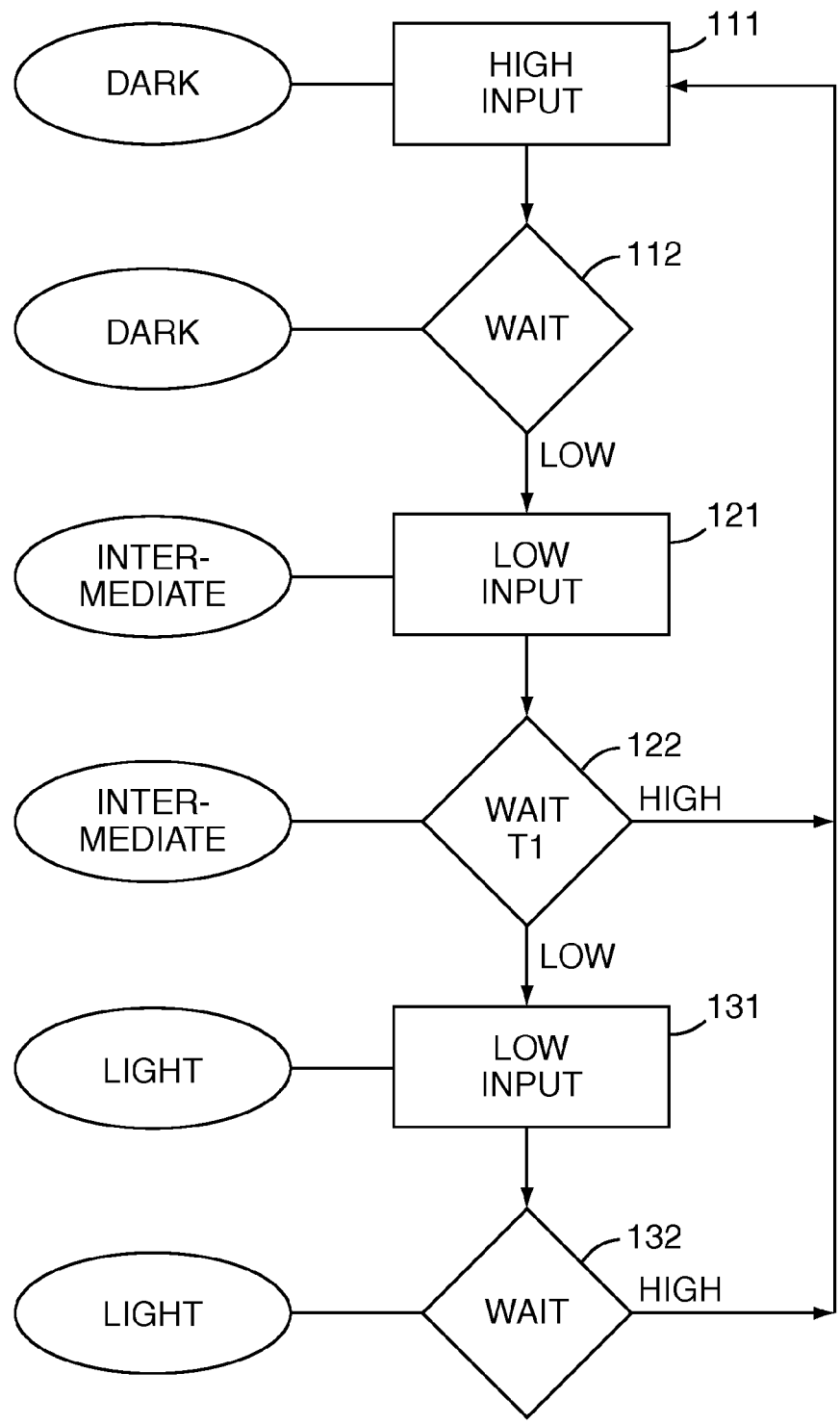
FIG. 3 is a flowchart illustrating the functioning of the apparatus and method of one embodiment of an automatic darkening filter apparatus.

With reference to FIG. 3, one operation 111 that system 16 can perform is that upon detection (via detector 18) of a change from high input to low input, system 16 immediately switches shutter 20 to a dark state. (In this context, immediately means as rapidly as the response time of the shutter allows. For many shutters, such response time typically will be less than one millisecond.) After execution of operation 111, upon continued detection of high input, system 16 executes waiting operation 112, in which shutter 20 is maintained in a dark state indefinitely upon continued detection of high input.

If, during waiting operation 112, system 16 detects a change from high input to low input, system 16 executes operation 121 and switches shutter 20 to an intermediate state. After execution of operation 121, system 16 executes waiting operation 122, in which system 16 holds shutter 20 in an intermediate state for a predetermined length of time $T_1$. If, at any time during length of time $T_1$ of waiting operation 122, a change from low input to high input is detected, system 16 terminates waiting operation 122 and executes operation 111 and switches shutter 20 to a dark state, as described above. Or, if at the end of time period $T_1$ a low input is still detected, system 16 executes operation 131 discussed below.

In various embodiments, predetermined time period $T_1$ is at least about 100 milliseconds long, at least about 300 milliseconds long, or at least about 500 milliseconds long. In various embodiments, time period $T_1$ is at most about 3.0 seconds, at most about 2.0 seconds, or at most about 1.0 second long. In one embodiment, time period $T_1$ is constant. In another embodiment, time period $T_1$ is adjustable by the user of automatic darkening filter apparatus 14 (e.g., by way of a switch or control built into system 16). In still another embodiment, time period $T_1$ is adjustable by system 16. For example, system 16 can comprise logic circuits that can monitor the average length of time of interruptions in high intensity light incidence, and adjust $T_1$ accordingly. In a specific example, if system 16 determines that an average interruption is around one second in length, $T_1$ can be set to at or over one second.

Operation 131, which is executed by system 16 upon the continued detection of low input at the end of length of time $T_1$, switches shutter 20 to a light state. After execution of operation 131, upon the continued detection of low input, system 16 will execute waiting operation 132 and maintain shutter 20 in a light state. This will continue until a change from low input to high input is detected (in which case above-described operation 111 is carried out), or automatic darkening filter apparatus 14 is turned off (not shown in FIG. 3). Operation of automatic darkening filter apparatus 14 may also include a power-on operation, also not shown in FIG. 3.

Figure 4:
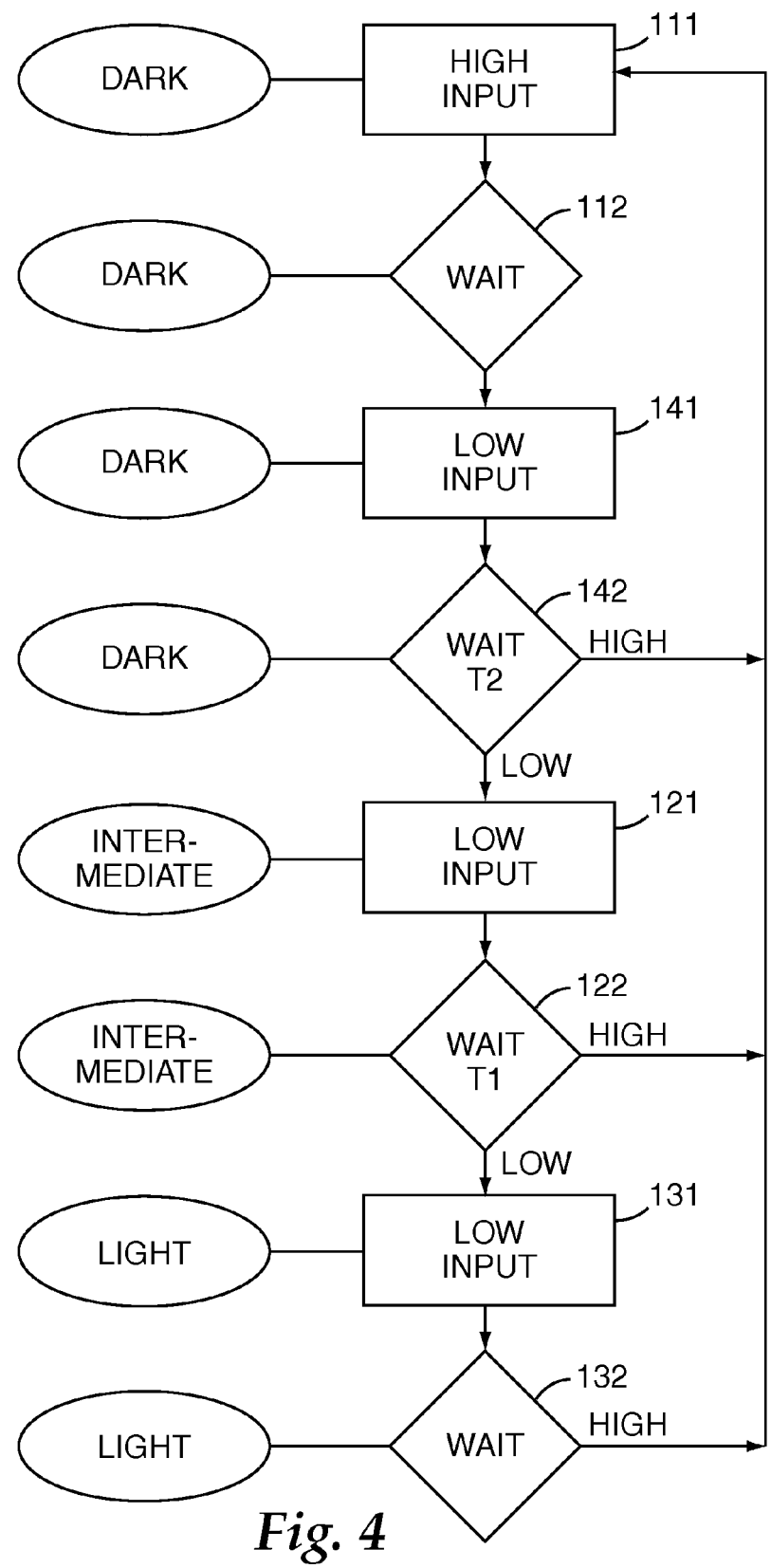
FIG. 4 is a flowchart illustrating the functioning of the apparatus and method of another embodiment of an automatic darkening filter apparatus.

An alternative embodiment of the functioning of system 16 is illustrated in an exemplary manner in FIG. 4. In this embodiment, system 16 functions in generally the same manner as in the embodiment of FIG. 3, with added operations 141 and 142. Specifically, during waiting operation 112, if system 16 detects a change from high input to low input, system 16 executes operation 141 and causes shutter 20 to remain in a dark state (rather than executing operation 121 and switching the shutter to an intermediate state as in the embodiment of FIG. 3). After executing operation 141, upon continued detection of low input system 16 executes waiting operation 142, in which system 16 holds shutter 20 in a dark state for a predetermined length of time $T_2$. If, at any time during length of time $T_2$, a change from low input to high input is detected, system 16 terminates waiting operation 142 and executes operation 111 (which maintains shutter 20 in a dark state). Or, if at the end of time period $T_2$ a low input is still detected, system 16 executes operation 121 and switches shutter 20 to an intermediate state. Upon carrying out operation 121, functioning of system 16 continues as described in the embodiment of FIG. 3.

The providing of a wait time $T_2$ thus provides that shutter 20 is maintained in a dark state for a period of time $T_2$ after high intensity light ceases to be detected. This delay period can combine with the above-described wait time $T_1$ to provide further beneficial effects for a user. In various embodiments, $T_2$ can be at least about 20 milliseconds, at least about 40 milliseconds, or at least about 60 milliseconds. In various embodiments, $T_2$ can be at most about 150 milliseconds, at most about 120 milliseconds, or at most about 90 milliseconds.

In the functioning of shutter control system 16 in use of automatic darkening filter 14 to block high intensity light, any or all of the various operations described above may be performed multiple times. The occurrence, order and/or duration of such operations may vary depending on the nature of the light being blocked (for example, in response to the frequency and length of the interruptions that occur in the course of intermittent welding operations). For example, if repeated interruptions in high intensity light occur, with such interruptions being of a duration shorter than time period $T_1$, operations 111/112, and operations 121/122, may be performed repeatedly (as may operations 141/142), with operation 131 only being performed when an interruption longer than $T_1$ is encountered (for example, at the end of a welding procedure). Such an exemplary sequence of operations is illustrated in the Example below.

In one embodiment, automatic darkening filter apparatus 14 can be configured such that a user can select between operating apparatus 14 in a mode in which shutter 20 is switched from a dark state to an intermediate state if a change from high input to low input is detected, and operating apparatus 14 in a mode in which the shutter is switched from a dark state directly to a light state (without being switched to and maintained in an intermediate state before being switched to the light state) if a change from high input to low input is detected. For example, a switch or other control mechanism may be provided in shutter control system 16 that allows such selection to be made.

The invention is more fully illustrated by way of the following example.

EXAMPLE

Figure 5:
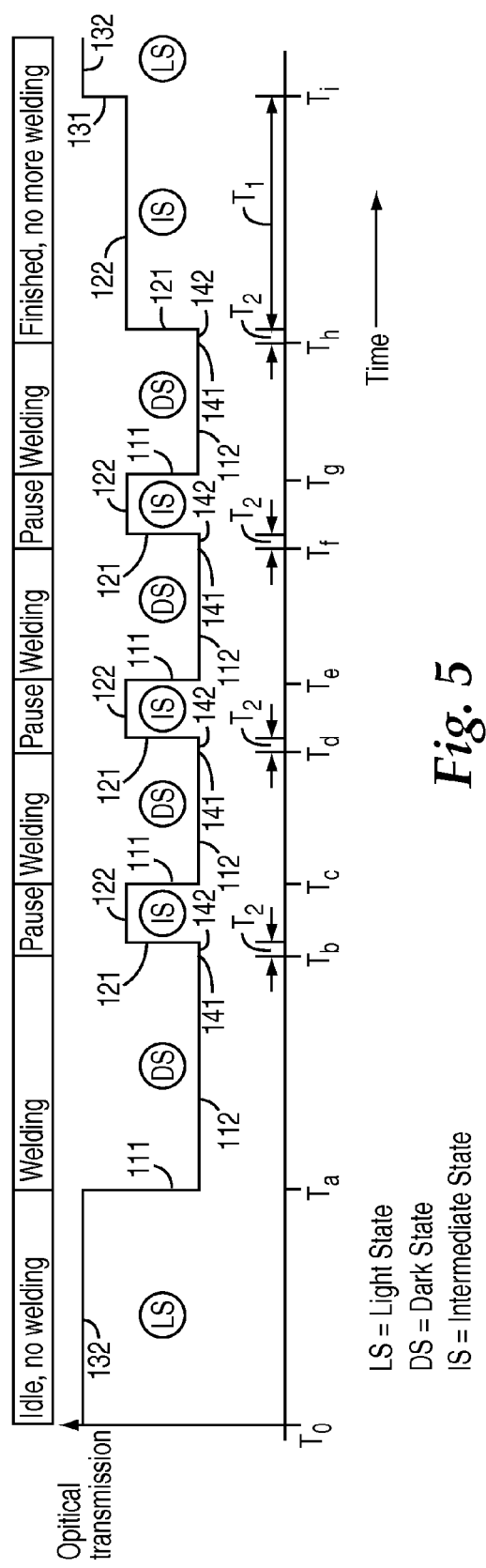
FIG. 5 illustrates the operation of an automatic darkening filter apparatus.
Figure 5:
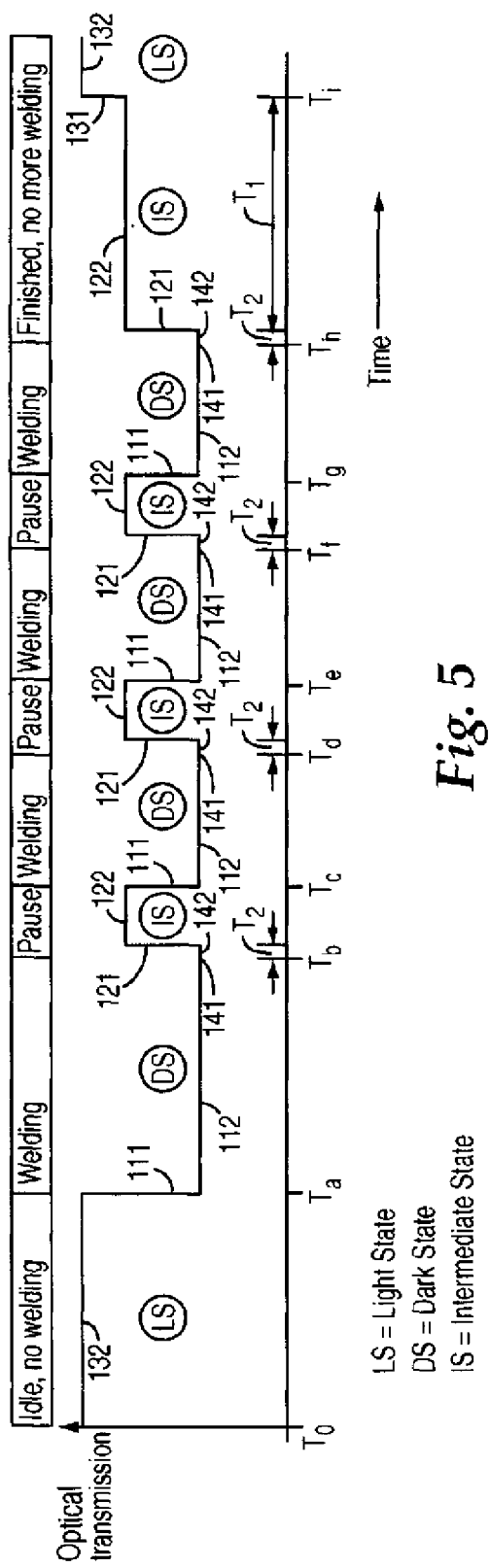

Operation of automatic darkening filter apparatus 14 is illustrated in an exemplary manner in FIG. 5. In this figure, the X axis represents time (units not shown) and the Y axis represents the optical transmission (units not shown) of a shutter 20. (The scale of the Y axis is for illustrative purposes only and is not intended to signify a quantitative relationship between the transmittance/opacity of shutter 20 in the various states.) The banner across the top of FIG. 5 indicates the status of a high-intensity light-emitting device 50 (in this case, a welding device) at various times. The circled symbols indicate the state of shutter 20 (light, dark or intermediate, as noted in the figure legend) at various times. The numbers correspond to various operations (with reference to FIGS. 3 and 4) executed by shutter control system 16. It should be noted that although some operations in FIG. 5 (e.g., 111, 121, and 131) are shown as being "instantaneous" (e.g., are represented by vertical line segments), such representations are so depicted for ease of presentation. In actual operation of automatic darkening filter 14, these operations will occur according to the response time of the shutter, as explained previously herein.

In proceeding from left to right in FIG. 5, at the start ($T_o$), device 50 is in an idle state (not emitting light) and shutter 20 is in a light state. (With reference to FIG. 4, shutter control system 16 is at this point detecting low input and executing waiting operation 132.)

At time $T_a$, device 50 emits high intensity light, thus system 16 detects a change from low input to high input, causing system 16 to execute operation 111 thus switching shutter 20 to a dark state. System 16 then executes waiting operation 112 during which shutter 20 is maintained in a dark state.

At time $T_b$, device 50 ceases to emit high intensity light, thus system 16 detects a change from high input to low input, causing system 16 to execute operation 141 (wherein shutter 20 is maintained in a dark state), followed by waiting operation 142 (wherein shutter 20 is maintained in a dark state). At the end of time period $T_2$, system 16 still detects low input, so system 16 executes operation 121 thus switching shutter 20 to an intermediate state. System 16 then executes waiting operation 122. At time $T_c$ (with wait time $T_1$ not having elapsed), device 50 resumes emitting high intensity light and system 16 detects a change from low input to high input, so system 16 executes operation 111 thus switching shutter 20 to a dark state. System 16 then executes waiting operation 112 during which shutter 20 is maintained in a dark state.

At time $T_d$, device 50 again ceases to emit high intensity light, thus system 16 detects a change from high input to low input, causing system 16 to execute operation 141 (wherein shutter 20 is maintained in a dark state), followed by waiting operation 142 (wherein shutter 20 is maintained in a dark state). At the end of time period $T_2$, system 16 still detects low input, so system 16 executes operation 121 thus switching shutter 20 to an intermediate state. System 16 then executes waiting operation 122. At time $T_e$ (with wait time $T_1$ not having elapsed), device 50 resumes emitting high intensity light and system 16 detects a change from low input to high input, so system 16 executes operation 111 thus switching shutter 20 to a dark state. System 16 then executes waiting operation 112 during which shutter 20 is maintained in a dark state.

At time $T_f$, device 50 again ceases to emit high intensity light, thus system 16 detects a change from high input to low input, causing system 16 to execute operation 141 (wherein shutter 20 is maintained in a dark state), followed by waiting operation 142 (wherein shutter 20 is maintained in a dark state). At the end of time period $T_2$, system 16 still detects low input, so system 16 executes operation 121 thus switching shutter 20 to an intermediate state. System 16 then executes waiting operation 122. At time $T_g$ (with wait time $T_1$ not having elapsed), device 50 resumes emitting high intensity light and system 16 detects a change from low input to high input, so system 16 executes operation 111 thus switching shutter 20 to a dark state. System 16 then executes waiting operation 112 during which shutter 20 is maintained in a dark state.

At time $T_h$, device 50 again ceases to emit high intensity light, thus system 16 detects a change from high input to low input, causing system 16 to execute operation 141 (wherein shutter 20 is maintained in a dark state), followed by waiting operation 142 (wherein shutter 20 is maintained in a dark state). At the end of time period $T_2$, system 16 still detects low input, so system 16 executes operation 121 thus switching shutter 20 to an intermediate state. System 16 then executes waiting operation 122. At time $T_i$ (with wait time $T_1$ having elapsed), system 16 still detects low input, so system 16 executes operation 131 thus switching shutter 20 to a light state. System 16 then executes waiting operation 132 and thus remains in (indefinite) wait time until a high input is received or automatic darkening filter apparatus 14 is powered off.

A number of embodiments of the invention have been described. Nevertheless, it will be understood that various modifications may be made without departing from the invention. Accordingly, other embodiments are within the scope of the following claims.

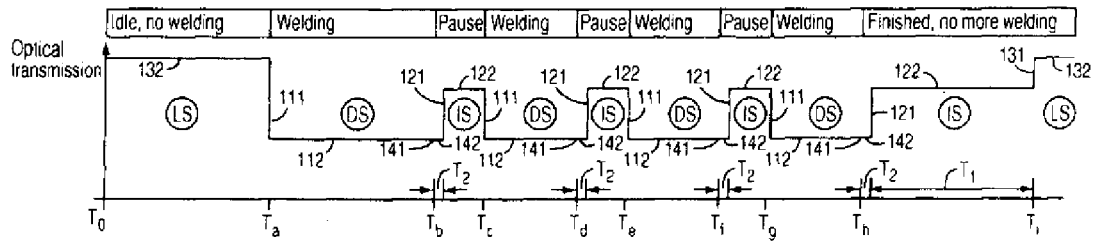

What is claimed is:

1. An automatic darkening filter apparatus comprising:
   a switchable shutter capable of assuming a dark state, a light state, and at least one intermediate state; and,
   a shutter control system operatively connected to the shutter and capable of detecting at least high input and low input and changes therebetween, wherein the shutter control system is configured to:
   switch the shutter from a dark state to an intermediate state if a change from high input to low input is detected;
   maintain the shutter in the intermediate state for a predetermined period of time $T_1$ of at least about 100 milliseconds if low input continues to be detected during period of time $T_1$;
   switch the shutter from the intermediate state to a light state at the end of period of time $T_1$ if low input is detected at the end of period of time $T_1$;
   switch the shutter to a dark state if a change from low input to high input is detected;
   maintain the shutter in the dark state if high input continues to be detected.

2. The apparatus of claim 1 wherein the shutter control system is further configured to maintain the shutter in a dark state for a predetermined period of time $T_2$ of greater than about 20 milliseconds if a change from high input to low input is detected, before switching the shutter from the dark state to an intermediate state.

3. The apparatus of claim 2 wherein period of time $T_2$ is less than about 2.0 seconds.

4. The apparatus of claim 1 wherein $T_1$ is at least about 500 milliseconds.

5. The apparatus of claim 1 wherein period of time $T_1$ is less than about 3.0 seconds.

6. The apparatus of claim 1 wherein period of time $T_1$ is less than about 2.0 seconds.

7. The apparatus of claim 1 wherein period of time $T_1$ is adjustable by a user of the apparatus.

8. The apparatus of claim 1 wherein period of time $T_1$ is adjustable by the shutter control system.

9. The apparatus of claim 1 wherein the automatic darkening filter apparatus is configured such that a user can select between operating the automatic darkening filter apparatus in a mode in which the shutter is switched from a dark state to an intermediate state if a change from high input to low input is detected, and operating the automatic darkening filter apparatus in a mode in which the shutter is switched from a dark state directly to a light state, without being switched to and maintained in an intermediate state before being switched to the light state, if a change from high input to low input is detected.

10. The apparatus of claim 1 wherein the shutter is positioned on or within a shield.

11. The apparatus of claim 1 wherein the switchable shutter is positioned on or within a shield of a protective headgear.

12. The apparatus of claim 1 wherein the switchable shutter comprises one or more liquid crystal layers.

13. The apparatus of claim 1 wherein the switchable shutter comprises a combination of layers of liquid crystals and polarizing filters.

14. The apparatus of claim 1 wherein the switchable shutter comprises an electrochromic material.

15. The apparatus of claim 1 wherein when the switchable shutter is in the dark state it exhibits a visible light transmission of less than about 0.5%.

16. The apparatus of claim 1 wherein when the switchable shutter is in the light state it exhibits a visible light transmission of greater than about 10%.

17. The apparatus of claim 1 wherein when the switchable shutter is in the intermediate state it exhibits a visible light transmission that is greater than about 1% and that is less than about 5%.

18. The apparatus of claim 1 wherein when the switchable shutter is in the intermediate state it exhibits a visible light transmission that is greater than about 1.5% and that is less than about 2%.

19. The apparatus of claim 1 wherein the shutter control system is configured such that a user can select between an operating mode in which the switchable shutter is switched from a dark state to an intermediate state if a change from high input to low input is detected, and an operating mode in which the switchable shutter is switched from a dark state directly to a light state, without being switched to and maintained in an intermediate state before being switched to the light state, if a change from high input to low input is detected.

* * * * *

UNITED STATES PATENT AND TRADEMARK OFFICE
CERTIFICATE OF CORRECTION

| | | |
|---|---|---|
| PATENT NO. | : 8,537,294 B2 | Page 1 of 3 |
| APPLICATION NO. | : 13/747541 | |
| DATED | : September 17, 2013 | |
| INVENTOR(S) | : Sundell | |

It is certified that error appears in the above-identified patent and that said Letters Patent is hereby corrected as shown below:

The title page showing the illustrative figure should be deleted to be replaced with the attached title page.

On the title page, item (72), Line 1, Delete "Laksand" and insert -- Leksand --, therefor.

In the Drawings:

The drawing sheet, consisting of Fig. 5, should be deleted to be replaced with the drawing sheet, consisting of Fig. 5, as shown on the attached pages.

Signed and Sealed this
Fifth Day of August, 2014

Michelle K. Lee
*Deputy Director of the United States Patent and Trademark Office*

(12) United States Patent
Sundell

(10) Patent No.: US 8,537,294 B2
(45) Date of Patent: Sep. 17, 2013

(54) AUTOMATIC DARKENING FILTER APPARATUS AND METHOD

(71) Applicant: 3M Innovative Properties Company, St. Paul, MN (US)

(72) Inventor: Ingvar Sundell, Laksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/747,541

(22) Filed: Jan. 23, 2013

(65) Prior Publication Data

US 2013/0128135 A1  May 23, 2013

Related U.S. Application Data

(62) Division of application No. 12/681,672, filed as application No. PCT/US2008/075089 on Sep. 3, 2008, now Pat. No. 8,384,855.

(60) Provisional application No. 60/977,701, filed on Oct. 5, 2007.

(51) Int. Cl.
  *G02F 1/1335* (2006.01)
(52) U.S. Cl.
  USPC .................................. 349/16; 349/96
(58) Field of Classification Search
  USPC ........................................... 349/96
  See application file for complete search history.

(56) References Cited

U.S. PATENT DOCUMENTS

| | | | |
|---|---|---|---|
| 5,208,688 A | 5/1993 | Fergason et al. | |
| 5,248,880 A | 9/1993 | Fergason | |
| 5,377,032 A | 12/1994 | Fergason et al. | |
| 5,519,522 A | 5/1996 | Fergason | |
| 5,751,258 A | 5/1998 | Fergason et al. | |
| 6,070,264 A | 6/2000 | Hamilton et al. | |
| 6,614,409 B1 | 9/2003 | Bae | |
| 6,881,939 B1 | 4/2005 | Hamilton et al. | |
| 6,884,987 B2 | 4/2005 | Hamilton et al. | |
| 7,005,624 B2 | 2/2006 | Hamilton | |
| 7,008,055 B2 | 3/2006 | McLear et al. | |
| 7,161,135 B2 | 1/2007 | Fergason | |
| 7,232,988 B2 | 6/2007 | Hamilton et al. | |
| 2003/0206491 A1 | 11/2003 | Pacheco et al. | |
| 2005/0007667 A1 | 1/2005 | Fergason | |
| 2006/0203148 A1 | 9/2006 | Magnusson et al. | |

FOREIGN PATENT DOCUMENTS

| | | |
|---|---|---|
| CN | 2 662 865 | 12/2004 |
| WO | WO 91/09337 A1 | 6/1991 |
| WO | WO 92/14183 A1 | 8/1992 |
| WO | WO 2005/051254 | 9/2005 |
| WO | WO 2007001777 | 1/2007 |

OTHER PUBLICATIONS

Supplementary European Search Report, PCT/US2008/075089, Sep. 29, 2010. 3 pages.

*Primary Examiner* — Phu Vu
(74) *Attorney, Agent, or Firm* — Kenneth B. Wood

(57) ABSTRACT

Herein is disclosed an automatic darkening filter apparatus comprising a shutter control system configured to cause a shutter to switch from a dark state to an intermediate state in response to a change from high intensity incident light to low intensity incident light being detected. The control system is further configured to maintain the shutter in the intermediate state for a period of time, unless during this period of time high intensity light is detected, in which case the control system causes the shutter to switch to the dark state. If, at the end of the period of time, high intensity light is not detected, the shutter is caused to switch from the intermediate state to a light state.

19 Claims, 4 Drawing Sheets